US00PP20712P2

(12) United States Plant Patent
Meilland

(10) Patent No.: US PP20,712 P2
(45) Date of Patent: Feb. 2, 2010

(54) MINIATURE ROSE PLANT NAMED 'MEIHANDICA'

(50) Latin Name: *Rosa hybrida*
Varietal Denomination: Meihandica

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 0 days.

(21) Appl. No.: 12/285,835

(22) Filed: Oct. 15, 2008

(30) Foreign Application Priority Data

Oct. 9, 2008 (EM) ..... 2008/2233

(51) Int. Cl.
*A01H 5/00* (2006.01)

(52) U.S. Cl. ..... Plt./119

(58) Field of Classification Search ..... Plt./119, Plt./118
See application file for complete search history.

*Primary Examiner*—Kent L Bell
(74) *Attorney, Agent, or Firm*—Buchanan Ingersoll & Rooney PC

(57) ABSTRACT

A new and distinct Miniature rose plant is provided which abundantly forms in clusters attractive cup-shaped blossoms that are ochre in coloration. A compact, low and bushy growth habit is displayed. The plant is well adapted for forcing in pot culture. The rather dense semi-glossy green foliage contracts nicely with the ochre blossom coloration. The new variety tends to blossom very early and on a nearly continuous basis thereafter. The tolerance to diseases is good, particularly with respect to Oidium. The new variety is well suited for providing attractive ornamentation in the landscape and when grown in pots.

1 Drawing Sheet

Figures 1, 2, 3, 4, 5, 6, 7, 8, 9, 10, 11, 12, 13, 14, 15, 16:
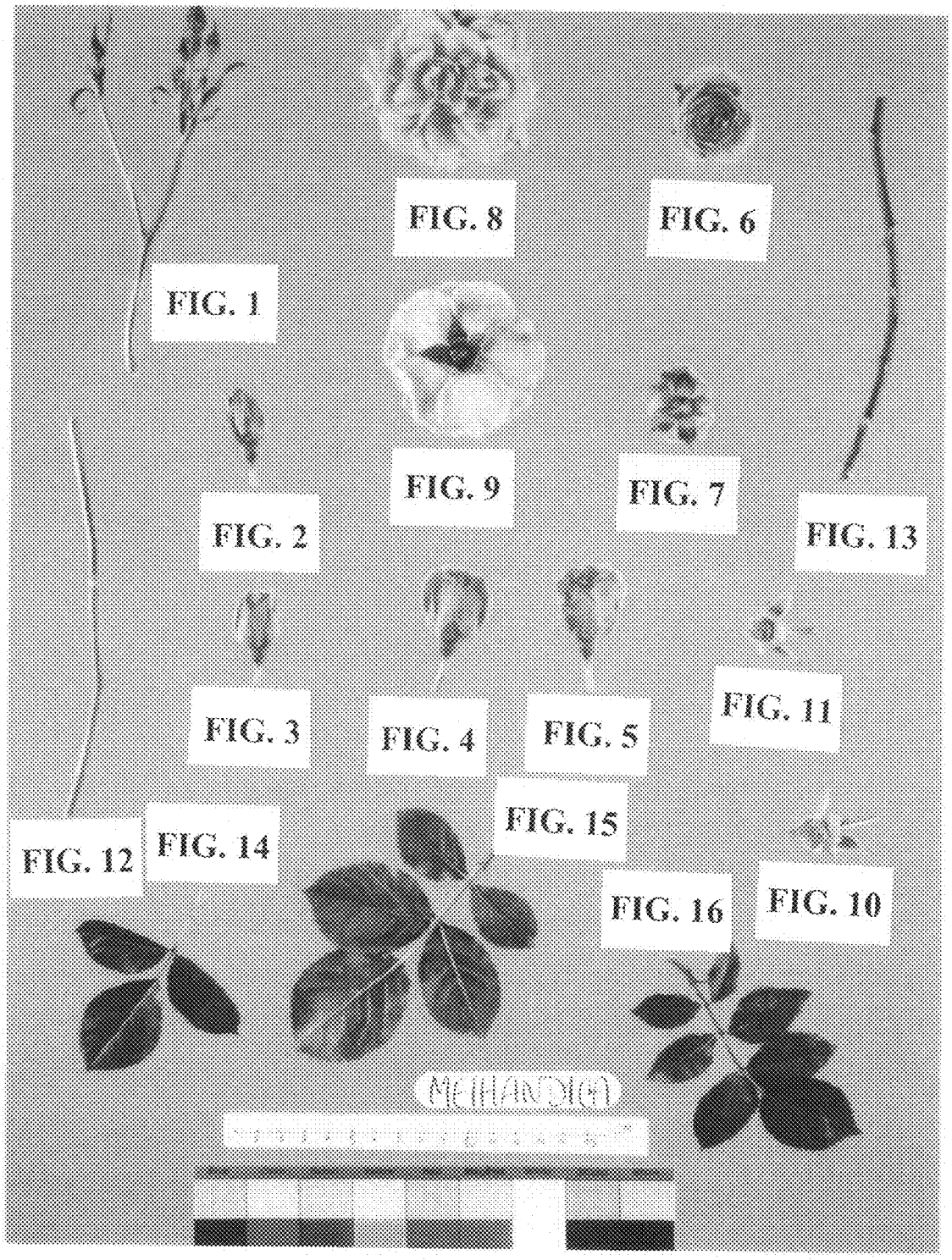

Botanical/commercial classification: *Rosa hybrida*/Miniature Rose Plant.

Varietal denomination: cv. Meihandica.

SUMMARY OF THE INVENTION

The new variety of *Rosa hybrida* Miniature rose plant was created by artificial pollination wherein two parents were crossed which previously had been studied in the hope that they would contribute the desired characteristics. The female parent (i.e., the seed parent) of the new variety was the product of the cross of the 'Meineyta' variety (non-patented in the United States) and an unnamed and unreleased seedling (non-patented in the United States). The male parent (i.e., the pollen parent) was the product of the cross of the 'Meichanso' variety (non-patented in the United States) and an unnamed and unreleased seedling (non-patented in the United States). The 'Meineyta' variety is marketed under the CUMBA MEILLANDIA trademark. The 'Meichanso' variety sometimes is known as the 'Parador' variety. The parentage of the new variety can be summarized as follows:

('Meineyta'×Unnamed Seedling)×('Meichanso'×Unnamed Seedling).

The seeds resulting from the above pollination were sown and small plants were obtained which were physically and biologically different from each other. Selective study resulted in the identification of a single plant of the new variety.

It was found that the new variety of Miniature rose plant of the present invention displays the following combination of characteristics:

(a) exhibits a compact, low and bushy growth habit and is well adapted for forcing in pot culture, (b) abundantly forms in clusters on a nearly continuous basis attractive cup-shaped blossoms that are ochre in coloration, (c) forms attractive rather dense semi-glossy green foliage, and (d) is well suited for providing attractive ornamentation.

The new variety well meets the needs of the horticultural industry. The new variety tends to blossom very early and nearly continuously thereafter. It can be grown in pots as well as in the landscape. For instance, it can be grown to advantage along walkways and in mixed border plantings. The semi-glossy green foliage contrasts well with the ochre blossom coloration.

The new variety of the present invention can be readily distinguished from its ancestors. The flower coloration is different in each instance. More specifically, the 'Meineyta' variety forms bicolored orange-yellow blossoms, and the 'Meichanso' variety forms Geranium Red flowers.

The new variety has been found to undergo asexual propagation in France by a number of routes, including budding, grafting, and cuttage. Asexual propagation by the above-mentioned methods as performed in the South of France has shown that the characteristics of the new variety are strictly transmissible from one generation to another.

The new variety has been named 'Meihandica'.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were approximately one year of age and were observed during May while growing outdoors on their own roots at LeCannet des Maures, Var, France. Dimensions in centimeters are shown at the bottom of the photograph, as well as a color comparison.

FIG. 1 — illustrates a specimen of a cluster of buds;

FIG. 2 — illustrates a specimen of a floral bud before the opening of the sepals;

FIG. 3 — illustrates a specimen of a floral bud at the opening of the sepals;

FIG. 4 — illustrates a specimen of a floral bud at the opening of the petals;

FIG. 5 — illustrates a specimen of a flower during the course of opening;

FIG. 6 — illustrates a specimen of a newly opened flower — plan view — obverse;

FIG. 7 — illustrates a specimen of a newly opened flower — plan view — reverse;

FIG. 8 — illustrates a specimen of a fully open flower — plan view — obverse;

FIG. 9 — illustrates a specimen of a fully open flower — plan view — reverse;

FIG. 10 — illustrates a specimen of a floral receptacle showing the arrangement of the stamens and pistils;

FIG. 11 — illustrates a specimen of a floral receptacle showing the arrangement of the pistils (stamens removed);

FIG. 12 — illustrates a specimen of a flowering stem;

FIG. 13 — illustrates a specimen of a main branch;

FIG. 14 — illustrates a specimen of a leaf with three leaflets — plan view — upper surface;

FIG. 15 — illustrates specimen of a leaf with five leaflets — plan view — under surface; and FIG. 16 — illustrates a specimen of a leaf with seven leaflets — plan view — upper surface.

DETAILED DESCRIPTION

The chart used in the identification of the colors is that of The Royal Horticultural Society (R.H.S. Colour Chart). The description is based on the observation of approximately one-year-old specimens of the new variety during May while growing on their own roots outdoors at LeCannet des Maures, Var, France.

Class: Miniature.

Plant:

*Habit.*—Compact, low and bushy.

*Height.*—Commonly approximately 30 cm on average.

*Width.*—Commonly approximately 30 cm on average.

Branches:

*Length.*—Commonly approximately 25 cm on average.

*Diameter.*—Commonly approximately 7 mm on average when mature.

Branches:

*Color.*—Young stems: near Yellow-Green Group 144A. adult wood: near Yellow-Green Group 146B.

*Thorns.*—Size and quantity: on young stems approximately 5 on average having a length of approximately 0.6 cm over a length of 10 cm. color: on young stems near Yellow-Green Group 146C. configuration: slightly curved downwards on the upper surface and slightly concave on the under surface, and with a substantially straight base.

Leaves:

*Petioles.*—Upper surface: non-glandular, and near Yellow-Green Group 148A in coloration. under surface: bear a few prickles, and near Yellow-Green Group 146C in coloration. size: commonly approximately 2.4 cm in length on average and approximately 1 to 2 mm in diameter on average on the terminal leaflet.

*Rachis.*—Upper surface: smooth, and near Yellow-Green Group 147A in coloration. under surface: smooth, and near Yellow-Green Group 146C in coloration. size: commonly approximately 2.4 cm in length on average, and approximately 0.5 mm in diameter on average.

*Stipules.*—Adnate, pectinate, narrow, approximately 1.8 cm in length on average, approximately 0.5 cm in width on average, near Green Group 143C on the upper surface, and near Green Group 143A on the under surface.

*Leaflets.*—Number: 3, 5 (most often), and 7. shape: elliptical, with a pointed cuspidate tip and an obtuse base (as illustrated). texture: rather thick. serration: small and single. general appearance: rather dense, medium green, and semi-glossy. size: terminal leaflets commonly measure approximately 4.3 cm in length on average and approximately 2.1 cm in width on average. color (young foliage). upper surface: near Green Group 141A. under surface: near Green Group 137C. color (mature foliage): upper surface: near Green Group 137A. under surface: near Yellow-Green Group 146C.

Inflorescence:

*Number of flowers.*—Commonly in clusters of flowers.

*Peduncle.*—Smooth, near Yellow-Green Group 143B in coloration, approximately 3.8 cm in length on average, and approximately 0.3 cm in diameter on average.

*Sepals.*—Number: five. upper surface: smooth, and near Green Group 139C in coloration. under surface: smooth, and near Green Group 143C in coloration. shape: longish-pointed, narrow, and three sepals commonly bear some longish foliaceous extensions having lengths of up to approximately 0.7 cm on average. length: approximately 2.5 cm on average. width: approximately 0.8 cm on average.

*Buds.*—Shape: ovoid. size: small, approximately 2.3 cm in length on average, and approximately 2 cm in width on average. color: as the calyx breaks on the upper surface near Orange Group 28A, and on the under surface near Orange-Red Group 30C.

*Flower.*—Form: double and cup-shaped. diameter: approximately 6 cm on average when fully open. depth: commonly approximately 2.4 cm on average when fully open. color (during the course of opening): upper surface: near Orange Group 26B, and suffused with Orange-Red Group 35C. under surface: near Orange-Red Group 31 C. color (when open). upper surface: near Yellow-Orange Group 23D, suffused with near Orange Group 28D, and Red Group 37C. under surface: Orange Group 27A suffused with near Orange Group 29D. discoloration: some lightening with age. fragrance: none. anthers: near Yellow-Orange Group 15A in coloration, regularly arranged around the styles, and approximately 0.3 cm in length on average. stamen number: approximately 39 on average. filaments: near Yellow Group 9B in coloration, and approximately 0.5 cm in length on average. pollen: present. pistil number: approximately 33 on average. stigmas: reddish in coloration, and approximately 0.5 cm in diameter on average. styles: near Yellow-Orange Group 19D in coloration, and approximately 0.5 cm in length. petal number: approximately 56 to 59 on average under normal growing conditions. petal arrangement: imbricated. petal shape: possess a cuneiform base and a rounded tip. petal margin: substantially uniform in configuration. petal size: approximately 3 cm in length on average, and approximately 2.5 cm in width on average. petal texture: relatively thick. petal drop: good, the petals commonly detach cleanly before drying. petaloids: small and commonly present primarily at the center. receptacle: smooth, near Yellow-Green Group 143A in coloration, pitcher-shaped in cross section, and approximately 0.5 cm in length on average and approximately 0.6 in width on average.

Development:

*Vegetation.*—Medium strong.

*Blooming.*—Very abundant and nearly continuous.

*Tolerance to diseases.*—Good, especially with respect to Oidium.

*Aptitude to forcing.*—Good.

I claim:

1. A new and distinct variety of Miniature rose plant characterized by the following combination of characteristics:

(a) exhibits a compact, low and bushy growth habit and is well adapted to forcing in pot culture, (b) abundantly forms in clusters on a nearly continuous basis attractive cup-shaped blossoms that are ochre in coloration, (c) forms attractive rather dense semi-glossy green foliage, and (d) is well suited for providing attractive ornamentation;

substantially as herein shown and described.

* * * * *

MEHANDIGI